(12) United States Patent
Lee et al.

(10) Patent No.: US 7,282,521 B2
(45) Date of Patent: Oct. 16, 2007

(54) ANTI-RETROVIRAL MORONIC ACID DERIVATIVES

(75) Inventors: Kuo-Hsiung Lee, Chapel Hill, NC (US); Fang-Rong Chang, Kaohsiung (TW); Yojiro Sakurai, Chapel Hill, NC (US); Chin Ho Chen, Chapel Hill, NC (US)

(73) Assignees: University of North Carolina at Chapel Hill, Chapel Hill, NC (US); Duke University, Durham, NC (US)

( * ) Notice: Subject to any disclaimer, the term of this patent is extended or adjusted under 35 U.S.C. 154(b) by 183 days.

(21) Appl. No.: 11/134,904

(22) Filed: May 23, 2005

(65) Prior Publication Data
US 2006/0004097 A1 Jan. 5, 2006

Related U.S. Application Data

(60) Provisional application No. 60/573,979, filed on May 24, 2004.

(51) Int. Cl.
*A61K 31/225* (2006.01)
*C07C 69/34* (2006.01)
(52) U.S. Cl. ...................... 514/548; 560/194
(58) Field of Classification Search ............... None
See application file for complete search history.

(56) References Cited

U.S. PATENT DOCUMENTS

| 5,468,888 | A | 11/1995 | Bouboutou et al. |
| 5,962,527 | A | 10/1999 | Pezzuto et al. |
| 6,048,847 | A | 4/2000 | Ramadoss et al. |
| 6,172,110 | B1 | 1/2001 | Lee et al. |
| 6,369,101 | B1 | 4/2002 | Carlson |
| 6,369,109 | B1 | 4/2002 | Debatin et al. |
| 6,458,834 | B2 | 10/2002 | Glinski et al. |
| 2004/0204389 | A1 | 10/2004 | Chen et al. |

OTHER PUBLICATIONS

International Search Report and Written Opinion for International Application No. PCT/US05/18036; Mailed Feb. 2, 2006.
Kurokawa, M. et al. Anti-Herpes Simplex Virus Activity of Moronic Acid Purified from *Rhus javanica* In Vitro and In Vivo. "The Journal of Pharmacology and Experimental Therapeutics" 289:72-78, 1999.
Ito, J., et al., "Anti-AIDS Agents. 48.[1] Anti-HIV Activity of Moronic Acid Derivatives and the New Melliferone-Related Triterpenoid Isolated from Brazilian Propolis," *J. Nat. Prod.* 64:1278-1281 (2001).

*Primary Examiner*—Paul A. Zucker
(74) *Attorney, Agent, or Firm*—Sterne, Kessler, Goldstein & Fox P.L.L.C.

(57) ABSTRACT

The present invention provides moronic acid derivatives of the general formula:

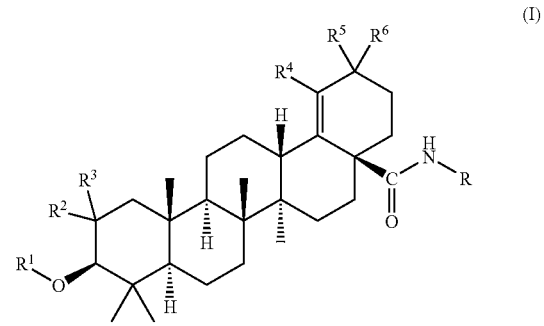

(I)

which have antiviral activity, along with compositions containing the same and methods of use thereof.

9 Claims, No Drawings

ANTI-RETROVIRAL MORONIC ACID DERIVATIVES

RELATED APPLICATIONS

This application claims the benefit of U.S. Provisional Patent Application Ser. No. 60/573,979 filed May 24, 2004, the disclosure of which is incorporated by reference herein in its entirety.

This invention was made with Government support under Grant No. AI-33066 from the National Institute of Health. The Government has certain rights to this invention.

FIELD OF THE INVENTION

The present invention concerns moronic acid derivatives, pharmaceutical formulations thereof, and methods of use thereof.

BACKGROUND OF THE INVENTION

The triterpenes constitute a promising class of anti-HIV agents. In our previous studies, two classes of anti-HIV betulinic acid derivatives exhibit very different anti-HIV profiles. IC9564 (1) and DSB (2) are examples of these two classes of anti-HIV agents. The class I compounds are betulinic acid with various C-28 amide modifications. The represent for this type of compound, IC9564 (1), the statine analog of betulinic acid, was found to be active at the early stage of viral infection (Sun, I. C; Chen, C. H.; Kashiwada, Y.; Wu, J. H.; Wang, H. K.; and Lee, K. H. Anti-AIDS Agents 49. Synthesis, Anti-HIV, and Anti-Fusion Activities of IC9564 Analogues Based on Betulinic Acid. *J. Med. Chem.* 2002, 45, 4271–4275; Holz-Smith, S. L.; Sun, I. C.; Jin, L.; Matthews, T. J.; Lee, K. H.; and Chen, C. H. Role of human immunodeficiency virus (HIV) type 1 envelope in the anti-HIV activity of the betulinic acid derivative IC9564. *Antimicrob. Agents Chemother.* 2001, 45, 60–66).

The class II anti-HIV agents are 3-acyl derivatives of betulinic acid. As an example, 3-O-(3',3'-dimethylsuccinyl)-betulinic acid (DSB, 2) was reported inhibiting HIV-1 maturation by interfering with HIV-1 P24/P2 processing, which results in a noninfectious HIV-1 particle (Kashiwada, Y.; Hashimoto, F.; Cosentino, L. M.; Chen, C. H.; Garrett, P. E.; and Lee, K. H. Betulinic Acid and Dihydrobetulinic Acid Derivatives as Potent Anti-HIV Agents. *J. Med. Chem.* 1996, 39, 1016–1017; Li, F.; Goila-gaur, R.; Salzwedel, K.; Kilgore, N. R.; Reddick, M.; Matallana, C.; Castillo, A.; Zoumplis, D.; Martin, D. E.; Orenstein, J. M.; Allaway, G. P.; Freed, E. O.; and Wild, C. T. PA-457: A potent HIV inhibitor that disrupts core condensation by targeting a late step in Gag processing. *Proc. Natl. Acad. Sci. U.S.A.* 2003, 100, 13555–13560).

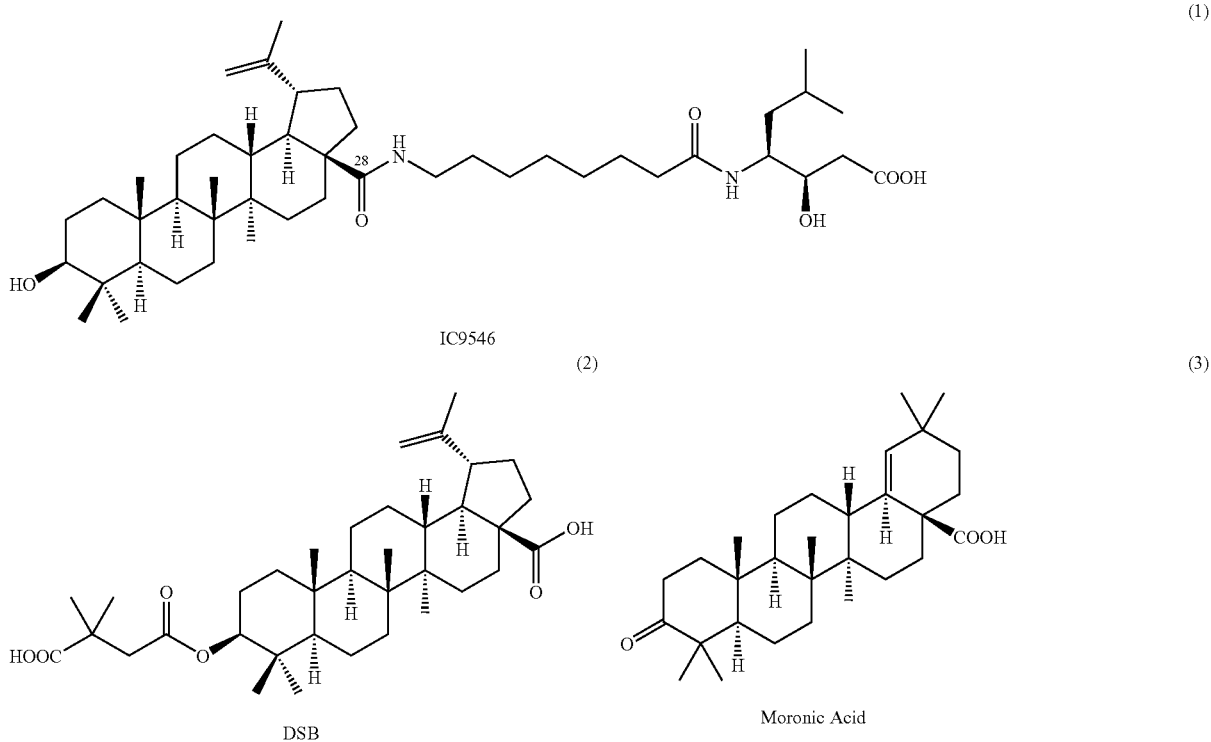

Among many class I modified C-28 amide compounds, a relatively long C-28 amide side chain is the common structure feature for relative potent anti-HIV entry activity. Compounds devoid of the C-28 side chain are totally inactive against HIV-1 entry (Hashimoto, F.; Kashiwada, Y.; Cosentino, L. M.; Chen, C. H.; Garrett, P. E.; and Lee, K. H. Anti-AIDS agents 27. Synthesis and anti-HIV activity of betulinic acid and dihydrobetulinic acid derivatives. *Bioorg. Med. Chem.* 1997, 5, 2133–2143). Replacing of the C28 amide group with methylene group or carboxyl ester led to activity loss (Evers, M.; Poujade, C.; Soler, F.; Ribeill, Y.;

James, C.; Lelievre, Y.; Gueguen, J. C.; Reisdorf, D.; and Morize, I. Betulinic Acid Derivatives: A New Class of Human Immunodeficiency Virus Type 1 Specific Inhibitors with a New Mode of Action. *J. Med. Chem.* 1996, 39, 1056–1068).

On the other hand, modifications on other parts of the betulin ring system do not significantly change their anti-HIV fusion activity. Modification of the 3-hydroxyl group with variety of acyl moiety does not significantly alter the anti-HIV entry profiles either. For class II BA derivatives, the most potent derivatives isovaleryl contain either 3,3-dimethyl-succinyl or glutaryl moieties at C-3. Terminal carboxylic acid domain in C-3 side chain is also required for potent anti-HIV activity (Sun, I. C.; Wang, H. K.; Kashiwada, Y.; Shen, J. K.; Cosentino, L. M.; Chen, C. H.; Yang, L. M.; and Lee, K. H. Anti-AIDS Agents. 34. Synthesis and Structure-Activity Relationships of Betulin Derivatives as Anti-HIV Agents. *J. Med. Chem.* 1998, 41, 4648–4657).

It was recently reported that betulinic acid derivatives with both C-3 and C-28 side chains possessed both anti-fusion and anti-maturation activity (Li, F.; Goila-gaur, R.; Salzwedel, K.; Kilgore, N. R.; Reddick, M.; Matallana, C.; Castillo, A.; Zoumplis, D.; Martin, D. E.; Orenstein, J. M.; Allaway, G. P.; Freed, E. O.; and Wild, C. T. PA-457: A potent HIV inhibitor that disrupts core condensation by targeting a late step in Gag processing. *Proc. Natl. Acad. Sci. U.S.A.* 2003, 100, 13555–13560; Huang, L.; Yuan, X.; Aiken, C.; and Chen, C. H. Bi-functional anti-HIV-1 small molecules with two novel mechanisms of action. *Antimicrob. Agents Chemother.* in press). Our previous papers reported that moronic acid (3), isolated from Brazilian propolis, also exhibited significant anti-HIV activity (EC$_{50}$<0.1 μg/mL, TI>186) in H9 lymphocyte (Ito, J.; Chang, F. R.; Wang, H. K.; Park, Y. K.; Ikegaki, M.; Kilgore, N.; and Lee, K. H. Anti-AIDS Agents. 48.Anti-HIV Activity of Moronic Acid Derivatives and the New Melliferone-Related Triterpenoid Isolated from Brazilian Propolis. *J. Nat. Prod.* 2001, 64, 1278–1281).

SUMMARY OF THE INVENTION

A first aspect of the present invention is a compound of Formula I:

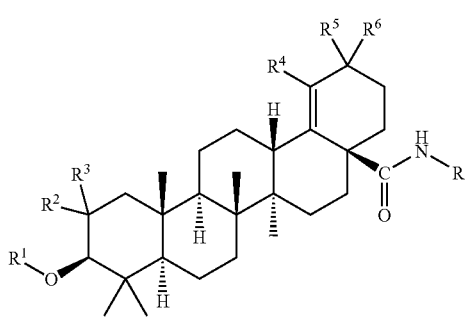

(I)

wherein:

R is a substituent of the formula:

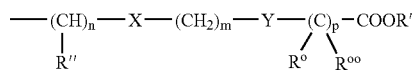

wherein:

R' and R" are the same or different, are hydrogen atoms or alkyl radicals,

X is a bond or represents a carbamoyl, N-methylcarbamoyl, aminocarbonyl or N-methylaminocarbonyl radical, Y is a bond or represents a phenylene radical, $R^o$ and $R^{oo}$ are the same or different, and are hydrogen atoms or alkyl radicals, or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X, it being possible for this ring to additionally comprise another hetero atom chosen from oxygen or sulphur and, n, m and p are each integers from 0 to 16, and m+n+p is between 4 and 16; or R is a substituent of the formula

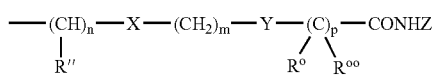

where R", $R^o$, $R^{oo}$, X, Y, n, m and p are as given above and Z is an amino acid radical joined to the adjacent nitrogen atom by a peptide bond to the amino terminus of the amino acid radical;

$R_1$ is a $C_2$ to $C_{20}$ substituted or unsubstituted carboxyacyl; or $R_1$ is a substituent of the formula

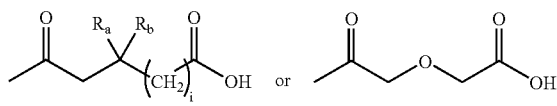

where $R_a$ and $R_b$ are the same or different and are each either hydrogen or loweralkyl, and i is an integer of from 0 to 3;

$R^2$ and $R^3$ are each hydrogen or together form an oxo radical;

$R^4$ is H or C1–C8 alkyl;

$R^5$ and $R^6$ are each either hydrogen or loweralkyl; or a pharmaceutically acceptable salt thereof. Such compounds are sometimes referred to as "active compounds" herein.

A further aspect of the present invention is a composition comprising an active compound as described herein in a pharmaceutically acceptable carrier (e.g., an aqueous solution).

A further aspect of the present invention is a method of treating a viral infection in a subject in need thereof, comprising administering to said subject an active compound as described herein in an amount effective to treat said viral infection.

A still further aspect of the present invention is the use of an active compound as described herein for the preparation of a medicament for the treatment of a viral infection as described herein.

The foregoing and other objects and aspects of the present invention are explained in greater detail below.

DETAILED DESCRIPTION OF THE PREFERRED EMBODIMENTS

"Acyl" as used herein means mean a —C(O)R radical, where R is a suitable substituent such as alkyl, alkoxy, alkenyl, alkynyl, aryl, etc., which may be substituted or unsubstituted (for example, an acetyl group, a propionyl group, a butyroyl group, a benzoyl group, or an alkylbenzoyl group).

"Alkyl," as used herein, refers to a straight or branched chain hydrocarbon, preferably containing from 1 to 4, 6 or 10 carbon atoms (with loweralkyl referring to C1 to C4 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

"Alkenyl" as used herein refers to an alkyl group as described above containing at least one carbon to carbon double bond.

"Alkynyl" as used herein refers to an alkyl group as described above containing at least one carbon to carbon triple bond.

"Carbamoyl" means the radical $NH_2CO-$, which may be substituted (by replacement of one or both H) or unsubstituted. (e.g., a substituted carbamoyl group with a substituent being an aliphatic group, an aromatic group, a heterocyclic residue, or the like and a carbamoyl group in which a ring is formed by connecting nitrogen atoms with each other; for example, a methylcarbamoyl group, a dimethylcarbamoyl group, an ethylcarbamoyl group, a diethyl carbamoyl group, a dibutylcarbamoyl group, a peperidinocarbamoyl group, a morpholinocarbamoyl group, a phenylcarbamoyl group, a methylphenylcarbamoyl group, an ethylphenylcarbamoyl group, a benzylphenylcarbamoyl group, etc.).

"Carboxy" as used herein means the radical —C(O)OH, which may in turn be substituted by replacement of H with another group.

"Amino acid" as used herein has its conventional meaning in the art and includes, but is not limited, to, amino acids with nonpolar R groups such as alanine, valine, leucine isoleucine, proline, phenylalanine, tryptophan, and methionine, amino acids with uncharged polar R groups such as glycine, serine, threonine, cysteine, tyrosine, asparagine, and glutamine, acidic amino acids (negatively charged at pH 6.0) such as aspartic acid and glutamic acid, basic amino acids (positively charged at pH 6.0) such as lysine, arginine, and histidine, as well as nonstandard amino acids such as ornithine, 2-napthylalanine, norvaline, norleucine, thienylalanine, 4-chlorophenylalanine, 3-benzothienyalanine, 4,4'-biphenylalanine, tetrahydro-isoquinoline-3-carboxylic acid, aminoisobutyric acid, alpha-aminonormalbutyric acid, 2,2-diphenylalanine, 4-thiazolylalanine, etc. Amino acids may be standard or naturally occurring amino acids, and may be alpha amino acids.

"Treat" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

1. Active Compounds.

The methods of the present invention include the administration of active compounds as described herein (e.g., compounds of Formula I), while pharmaceutical compositions of the present invention comprise active compounds in a pharmaceutically acceptable carrier or diluent.

Active compounds of the present invention include compounds of Formula I as follows:

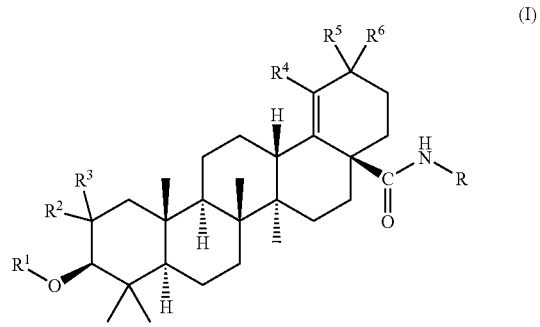

(I)

wherein:

R is a substituent of the formula:

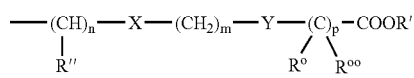

wherein:

R' and R" are the same or different, are hydrogen atoms or alkyl radicals,

X is a bond or represents a carbamoyl, N-methylcarbamoyl, aminocarbonyl or N-methylaminocarbonyl radical, Y is a bond or represents a phenylene radical, $R^o$ and $R^{oo}$ are the same or different, and are hydrogen atoms or alkyl radicals, or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X, it being possible for this ring to additionally comprise another hetero atom chosen from oxygen or sulphur and, n, m and p are each integers from 0 to 16, and m+n+p is between 4 and 16; or R is a substituent of the formula

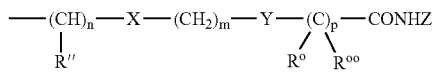

where R", $R^o$, $R^{oo}$, X, Y, n, m and p are as given above and Z is an amino acid radical joined to the adjacent nitrogen atom by a peptide bond to the amino terminus of the amino acid radical;

$R_1$ is a $C_2$ to $C_{20}$ substituted or unsubstituted carboxyacyl; or $R_1$ is a substituent of the formula

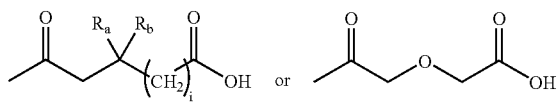

where $R_a$ and $R_b$ are the same or different and are each either hydrogen or loweralkyl, and i is an integer of from 0 to 3;

$R^2$ and $R^3$ are each hydrogen or together form an oxo radical;

$R^4$ is H or C1–C8 alkyl;

$R^5$ and $R^6$ are each either hydrogen or loweralkyl; or a pharmaceutically acceptable salt thereof. Such compounds are sometimes referred to as "active compounds" herein.

In some embodiments of the foregoing, $R^2$ and $R^3$ are each H.

In some embodiments of the foregoing, $R^4$ is H.

In some embodiments of the foregoing, $R^5$ and $R^6$ are each methyl.

Preferred embodiments of the foregoing include compounds of of Formula Ia:

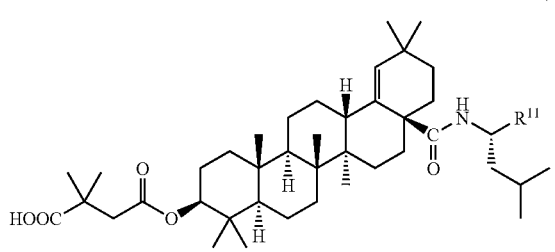

wherein:

$R^{11}$ is selected from the group consisting of —CH$_2$OH and —COOH;

or a pharmaceutically acceptable salt thereof.

The active compounds disclosed herein or described above can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 1 or 10 mg to about 100 milligrams, 1 gram or 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Methods of Treatment.

The present invention is primarily concerned with the treatment of human subjects, but the invention may also be carried out on animal subjects, particularly mammalian subjects such as mice, rats, dogs, cats, non-human primates, livestock and horses for veterinary purposes, and for drug screening and drug development purposes.

Examples of retroviral infections that may be treated by the methods of the present invention include but are not limited to feline leukemia virus (FeLV), human immunodeficiency virus (HIV; including both HIV-1 and HIV-2) simian immunodeficiency virus (SIV) and other lentiviral infections such as equine infectious anemia virus (EAIV) and feline immunodeficiency virus (FIV). A particularly preferred embodiment is use of the methods, compounds and compositions of the present invention for the treatment of HIV-1 infection in human subjects.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. Typical dosages comprise at about 0.1 to about 100 mg/kg body weight. One preferred dosages comprise about 1 to about 100 mg/kg body weight of the active ingredient. One still more preferred dosages comprise about 10 to about 100 mg/kg body weight.

4. Combination Methods and Compositions.

Methods of treatment as described herein can include concurrently administering one or more additional anti-viral agent, and compositions as described herein can optionally include one or more additional antiviral agents. Examples of such additional antiviral agents include, but are not limited to, AZT (Glaxo Wellcome), 3TC (Glaxo Wellcome), ddI (Bristol-Myers Squibb), ddC (Hoffmann-La Roche), D4T (Bristol-Myers Squibb), abacavir (Glaxo Wellcome), nevirapine (Boehringher Ingelheim), delavirdine (Pharmacia and Upjohn), efavirenz (DuPont Pharmaceuticals), saquinavir (Hoffmann-La Roche), ritonavir (Abbott Laboratories), indinavir (Merck and Company), nelfinavir (Agouron Pharmaceuticals), amprenavir (Glaxo Wellcome), adefovir (Gilead Sciences), hydroxyurea (Bristol-Meyers Squibb), AL-721 (lipid mixture) manufactured by Ethigen Corporation and Matrix Research Laboratories; Amphotericin B methyl ester; Ampligen (mismatched RNA) developed by DuPont/HEM Research; anti-AIDS antibody (Nisshon Food); 1 AS-101 (heavy metal based immunostimulant); Betaseron (.beta.-interferon) manufactured by Triton Biosciences (Shell Oil); butylated hydroxytoluene; Carrosyn (polymannoacetate); Castanospermine; Contracan (stearic acid derivative); Creme Pharmatex (containing benzalkonium chloride) manufactured by Pharmalec; CS-87 (5-unsubstituted derivative of Zidovudine), Cytovene (ganciclovir) manufactured by Syntex Corporation; dextran sulfate; D-penicillamine (3-mercapto-D-valine) manufactured by Carter-Wallace and Degussa Pharmaceutical; Foscarnet (trisodium phosphonoformate) manufactured by Astra AB; fusidic acid manufactured by Leo Lovens; glycyrrhizin (a constituent of licorice root); HPA-23 (ammonium-21-tungsto-9-antimonate) manufactured by Rhone-Poulenc Sante; human immune virus antiviral developed by Porton Products International; Ornidyl (eflornithine) manufactured by Merrell-Dow; nonoxinol; pentamidine isethionate (PENTAM-300) manufactured by Lypho Med; Peptide T (octapeptide sequence) manufactured by Peninsula Laboratories; Phenytoin (Warner-Lambert); Ribavirin; Rifabutin (ansamycin) manufactured by Adria Laboratories; CD4-IgG2 (Progenics Pharmaceuticals) or other CD4-containing or CD4-based molecules; T-20 (Trimeris); Trimetrexate manufactured by Warner-Lambert Company; SK-818 (germanium-derived antiviral) manufactured by Sanwa Kagaku;

suramin and analogues thereof manufactured by Miles Pharmaceuticals; UA001 manufactured by Ueno Fine Chemicals Industry; and alpha-interferon, manufactured by Glaxo Wellcome.

Pharmaceutical compositions of the present invention can also further comprise immunomodulators, and methods of treatment of the present invention can include the co-administration of an immunomodulator. Suitable immunomodulators for optional use with the active compounds of the present invention in accordance with the present invention can include, but are not limited to: ABPP (Bropririmine); Ampligen (mismatched RNA) DuPont/HEM Research; anti-human interferon-.alpha.-antibody (Advance Biotherapy and Concepts); anti-AIDS antibody (Nisshon Food); AS-101 (heavy metal based immunostimulant; ascorbic acid and derivatives thereof; interferon-.beta.; Carrosyn (polymannoacetate); Ciamexon (Boehringer-Mannheim); cyclosporin; cimetidine; CL-246,738 (American Cyanamid); colony stimulating factors, including GM-CSF (Sandoz, Genetics Institute); dinitrochlorobenzene; HE2000 (Hollis-Eden Pharmaceuticals); interferon-.alpha.; inteferon-gamma; glucan; hyperimmune gamma-globulin (Bayer); IMREG-1 (leukocyte dialyzate) and IMREG-2 (IMREG Corp.); immuthiol (sodium diethylthiocarbamate (Institut Merieux); interleukin-1 (Cetus Corporation; Hoffmann-LaRoche; Immunex); interleukin-2 (IL-2) (Chiron Corporation); isoprinosine (inosine pranobex); Krestin (Sankyo); LC-9018 (Yakult); lentinan (Ajinomoto/Yamanouchi); LF-1695 (Fournier); methionine-enkephalin (TNI Pharmaceuticals; Sigma Chemicals); Minophagen C; muramyl tripeptide, MTP-PE (Ciba-Geigy); naltrexone ("Trexan" DuPont); Neutropin, RNA immunomodulator (Nippon Shingaku); Remune (Immune Response Corporation); Reticulose (Advanced Viral Research Corporation); shosaikoto and ginseng; thymic humoral factor; TP-05 (Thymopentin, Ortho Pharmaceuticals); Thymosin factor 5 and Thymosin 1; Thymostimulin; TNF (Tumor necrosis factor) manufactured by Genentech; and vitamin B preparations.

The present invention is explained in greater detail in the following non-limiting Examples.

EXAMPLES 1–2

Compound Synthesis

In our continuing investigations, 3 was strategically modified for dual-function group based on the SAR of betulinic acid derivatives.

Chemistry: The methanol extract (600 g) of the propolis, collected by Africanized *Apis mellifera* in southern Brazil, gave 3 in good yield (1.5 g, 0.25%) (Ito, J.; Chang, F. R.; Wang, H. K.; Park, Y. K.; Ikegaki, M.; Kilgore, N.; and Lee, K. H. Anti-AIDS Agents. 48.Anti-HIV Activity of Moronic Acid Derivatives and the New Melliferone-Related Triterpenoid Isolated from Brazilian Propolis. *J. Nat. Prod.* 2001, 64, 1278–1281). The synthetic scheme of moronic acid derivatives (7 and 8) is shown in Scheme 1. Moronic acid (3) was first treated with oxalyl chloride to generate acid chloride 4, which was further reacted with leucine methyl ester hydrochloride and $Et_3N$ in $CH_2Cl_2$ overnight at room temperature to afford 5 in a yield of 89% for these two steps. To reduce the C-3 keto group of 5, sodium borohydride was added to the solution of 5 in MeOH and THF to produce 6a and 6b with yields of 60% and 33%, respectively. Compound 6b was hydrolyzed to 6c by treating with 2N KOH in MeOH and THF at 0° C. The 3β-hydroxyl group of 6a and 6c was reacted with 3,3-dimethylsuccinic anhydride and DMAP in pyridine to yield target final products, 7 and 8.

Scheme 1. Synthesis of moronic acid derivatives (7 and 8): (i) $(CO)_2Cl_2/CH_2Cl_2$; (ii) Leu-OMe, $Et_3N/CH_2Cl_2$; (iii) $NaBH_4$/MeOH/THF; (iv) 2N KOH/THF/MeOH; (v) 3,3-Dimethylsuccinic anhydride, DMAP/pyridine.

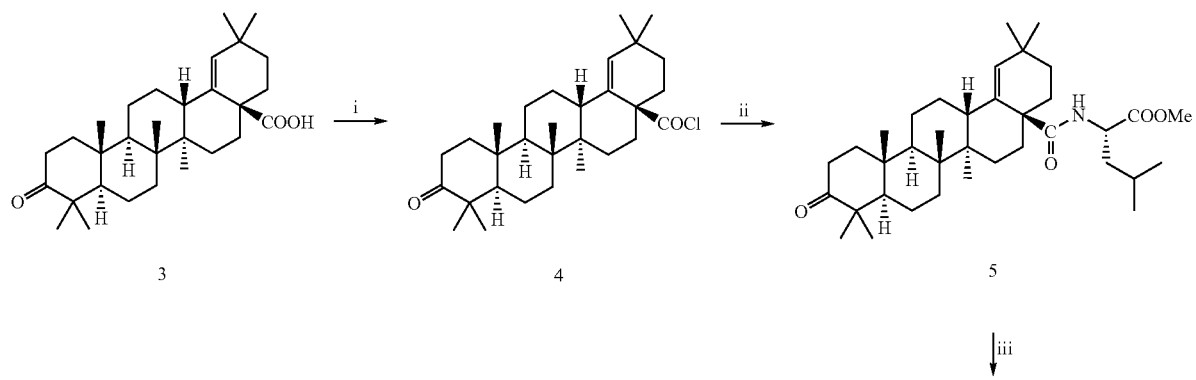

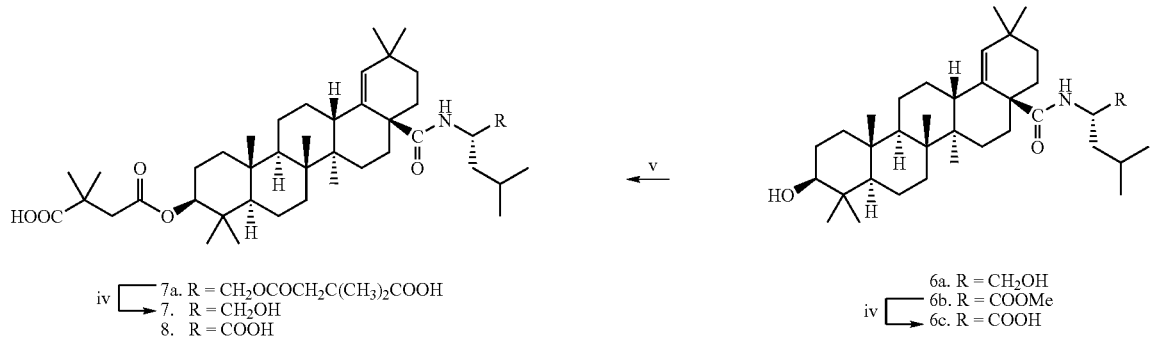

iv ⌈ 7a. R = CH₂OCOCH₂C(CH₃)₂COOH
   ⌊ 7. R = CH₂OH
     8. R = COOH iv ⌈ 6a. R = CH₂OH
   ⌊ 6b. R = COOMe
     6c. R = COOH

Analytical: N-[3β-(3',3'-Dimethylsuccinoxy)olean-18-en-28-oyl]-(1-hydroxy-methyl-3-methyl-butyl)-amide (7). Yield 70%; white amorphous powder; mp 237–238° C.; MS (ESI-) m/z: 682.8 (M⁺−1) for $C_{42}H_{69}O_6N$. $^1H$ NMR (300 MHz, $CDCl_3$) δ 0.76, 0.80, 0.83, 0.87, 0.97, 0.99 (6H) (3H each, s, $CH_3$-23, 24, 25, 26, 27, 29 and 30), 0.90, 0.92 (3H each, d, J=4.4 Hz, —CH($CH_3$)₂-28 side chain), 1.28 (6H, d, J=6.3 Hz, 2×$CH_3$-3'), 3.49 (1H, dd, J=10.8, 3.9 Hz, —CHCH₂OH-28 side chain), 3.64 (1H, dd, J=10.8, 6.3 Hz, —CH₂OH-28 side chain), 4.03 (1H, m, —NHCH—), 4.49 (1H, dd, J=9.9, 5.4 Hz, H-3), 5.34 (1H, s, H-19), 5.88 (1H, d, J=8.1 Hz, —CONH—).

N-[3β-(3',3'-Dimethylsuccinoxy)olean-18-en-28-oyl]-L-leucine (8). Yield 30%; white amorphous powder; mp 223–224° C.; MS (ESI-) m/z: 696.8 (M⁺−1) for $C_{42}H_{67}O_7N$. $^1H$ NMR (300 MHz, $CDCl_3$) δ 0.76, 0.77, 0.83, 0.85, 0.93 (6H), 1.03 (3H each, s, $CH_3$-23, 24, 25, 26, 27, 29 and 30), 0.99 (6H, d, J=7.2 Hz, —CH($CH_3$)₂-28 side chain), 1.30 (6H, d, J=8.4 Hz, 2×$CH_3$-3'), 4.52 (1H, dd, J=8.1, 4.8 Hz, H-3), 4.68 (1H, m, —NHCH—), 5.37 (1H, s, H-19), 6.32 (1H, d, J=8.1 Hz, —CONH—).

EXAMPLES 3–4

Antiretroviral Activity

Activity: Two moronic acid derivatives 7 and 8 were evaluated for their anti-HIV-1 replication activity against MT-4 cells, and the results were summarized in Table 1 ($IC_{50}$ is the concentration that inhibits uninfected H9 cell growth by 50%; $EC_{50}$ is the concentration that inhibits viral replication by 50%; and TI=$IC_{50}/EC_{50}$).

NL4-3 is a T-cell adapted HIV-1 strain, a wild type virus; PI—R is HIV-1M46I/L63P/V82P/I84V, an HIV-1 strain resistant to multiple protease inhibitors; and FHR-2 is an HIV-1 strain resistant to DSB (2). Compound 8, with leucine substituent on C-28, exhibited better activities in all three HIV-1 strains than 7. In NL4-3 strain, compound 8 showed an $EC_{50}$ value of 0.0057 μM, more active than 2, and compound 7 had an $EC_{50}$ value of 0.045 μM, similar to that of 2. Both 7 and 8 showed better activity ($EC_{50}$=0.088 and 0.021 μM) in multi-PI resistant strain than 2. As for the FHR-2 HIV-1 strain, which is resistant to 2, compound 8 remained some potency at $EC_{50}$ of 0.13 μM, however, compound 7 only showed weak activity ($EC_{50}$=2.78 μM).

Our preliminary results indicate that the moronic acid derivatives 7 and 8 also exhibit anti-HIV fusion activity (data not shown).

This modification study indicated that the betulinic acid scaffold can be replaced by an analogous triterpene, moronic acid, without loss of activity. Disubsituted moronic acid derivatives with both side chains on C-3 and C-28 are likely to have dual functions as we designed. In at least some embodiments they exhibited better drug resistance profiles than their parent compound 2. When reducing the carboxylic acid in the leucine, compound 7 showed less active in all testing viral strains than 8, therefore, it indicated the carboxylic acid within the leucine side chain is more favorable for target interaction. Additional modification SAR studies are in progress with an aim to continually improve potency in both viral strains.

TABLE 1

Anti-HIV activities of moronic acid derivatives (7, 8) in MT-4 cells.

| | Viral Stain | | | |
| Compound | NL4-3 [a] | PI-R [b] | FHR-2 [c] | $IC_{50}$ (μM) |
| --- | --- | --- | --- | --- |
| 7 | 0.045 | 0.088 | 2.78 | >14.6 |
| 8 | 0.0057 | 0.021 | 0.13 | >14.3 |
| DSB (2) | 0.096 | 0.43 | — | >5 |
| AZT | 0.013 | * | 0.19 | >37.5 |

[a] a T-cell adapted HIV-1 strain, X4 wild type virus.

[b] an HIV-1 strain, HIV-1M46I/L63P/V82P/I84V, resistant to multiple protease inhibitors.

[c] an HIV-1 strain resistant to DSB (2).

— No suppression at testing concentration, 5 μM.

* Did not include in the screening.

The foregoing is illustrative of the present invention, and is not to be construed as limiting thereof. The invention is defined by the following claims, with equivalents of the claims to be included therein.

That which is claimed is:

1. A compound of Formula I:

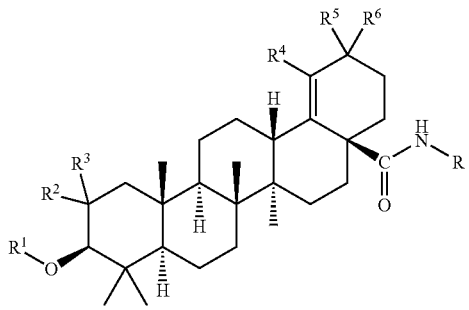

(I)

wherein:

R is a substituent of the formula:

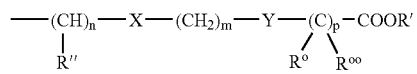

wherein:
- R' and R" are the same or different, are hydrogen atoms or alkyl radicals,
- X is a bond or represents a carbamoyl, N-methylcarbamoyl, aminocarbonyl or N-methylaminocarbonyl radical,
- Y is a bond or represents a phenylene radical,
- $R^o$ and $R^{oo}$ are the same or different, and are hydrogen atoms or alkyl radicals, or $R^o$ is hydroxyl, hydroxyalkyl, phenyl, benzyl, carbamoylmethyl or else, when Y is a bond and X is carbamoyl, $R^o$ can form a 5- or 6-membered ring with the nitrogen atom contained in X, it being possible for this ring to additionally comprise another hetero atom chosen from oxygen or sulphur and,
- n, m and p are each integers from 0 to 16, and m+n+p is between 4 and 16; or R is a substituent of the formula

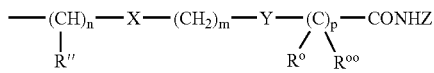

where R", $R^o$, $R^{oo}$, X, Y, n, m and p are as given above and Z is an amino acid radical joined to the adjacent nitrogen atom by a peptide bond to the amino terminus of the amino acid radical;

$R_1$ is a $C_2$ to $C_{20}$ substituted or unsubstituted carboxyacyl; or $R_1$ is a substituent of the formula

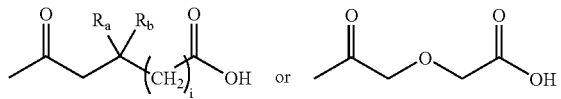

where $R_a$ and $R_b$ are the same or different and are each either hydrogen or loweralkyl, and i is an integer of from 0 to 3;

$R^2$ and $R^3$ are each hydrogen or together form an oxo radical;

$R^4$ is H or C1–C8 alkyl;

$R^5$ and $R^6$ are each either hydrogen or loweralkyl;

or a pharmaceutically acceptable salt thereof.

2. The compound of claim 1, wherein $R^2$ and $R^3$ are each H.

3. The compound of claim 1, wherein $R^4$ is H.

4. The compound of claim 1, wherein $R^5$ and $R^6$ are each methyl.

5. A compound of claim 1 having the structure of Formula Ia:

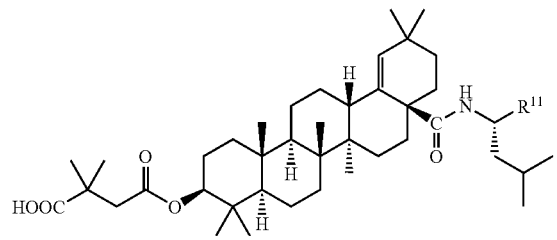

(Ia)

wherein:

$R^{11}$ is selected from the group consisting of —$CH_2OH$ and —COOH;

or a pharmaceutically acceptable salt thereof.

6. A composition comprising a compound of claim 1 in a pharmaceutically acceptable carrier.

7. The composition according to claim 6, wherein said carrier comprises an aqueous solution.

8. A method of treating a viral infection in a subject in need thereof, comprising administering to said subject a compound of Formula I as claimed in claim 1 in an amount effective to treat said retroviral infection.

9. The method of claim 8, wherein said viral infection is an HIV-1 infection.

* * * * *